United States Patent
Sekido

(10) Patent No.: US 8,437,144 B2
(45) Date of Patent: May 7, 2013

(54) LAMINATE MOUNT ASSEMBLY

(75) Inventor: Takanori Sekido, Machida (JP)

(73) Assignee: Olympus Corporation, Tokyo (JP)

( * ) Notice: Subject to any disclaimer, the term of this patent is extended or adjusted under 35 U.S.C. 154(b) by 240 days.

(21) Appl. No.: 12/942,236

(22) Filed: Nov. 9, 2010

(65) Prior Publication Data

US 2011/0226510 A1   Sep. 22, 2011

(30) Foreign Application Priority Data

Nov. 12, 2009   (JP) .................. 2009-259165

(51) Int. Cl.
*H05K 1/11*   (2006.01)

(52) U.S. Cl.
USPC ........... 361/803; 174/260; 361/742; 361/770; 361/804; 361/807

(58) Field of Classification Search .................. 361/728, 361/735, 736, 742, 768, 770, 790, 792, 793, 361/803, 804, 807–810, 767; 174/260–262
See application file for complete search history.

(56) References Cited

U.S. PATENT DOCUMENTS

| | | | | |
|---|---|---|---|---|
| 4,730,241 A * | 3/1988 | Takaya | ............................ | 363/19 |
| 5,847,930 A * | 12/1998 | Kazle | ............................ | 361/736 |
| 6,523,252 B1 * | 2/2003 | Lipponen | ........................ | 29/828 |
| 6,534,726 B1 * | 3/2003 | Okada et al. | .................. | 174/263 |
| 6,621,011 B1 * | 9/2003 | Daidai et al. | .................. | 174/258 |
| 6,862,190 B2 * | 3/2005 | Olzak et al. | .................... | 361/768 |
| 7,851,278 B2 * | 12/2010 | Nishi et al. | ..................... | 438/149 |
| 2006/0160379 A1 * | 7/2006 | Rathburn | ........................ | 439/66 |
| 2007/0279890 A1 * | 12/2007 | Motohara et al. | ............. | 361/810 |

FOREIGN PATENT DOCUMENTS

| JP | 08-279588 | 10/1996 |
|---|---|---|
| JP | 2008-168042 | 7/2008 |

* cited by examiner

*Primary Examiner* — Hoa C Nguyen
(74) *Attorney, Agent, or Firm* — Scully, Scott, Murphy & Presser, P.C.

(57) ABSTRACT

A laminate mount assembly includes a first member that includes an inter-member connection electrode that is provided on an end surface that forms a predetermined inter-member connection side surface; a second member that includes an inter-member connection electrode that is provided on an end surface that forms the inter-member connection side surface, the second member being arranged to be parallel with the first member; and a conductive film that electrically connects the inter-member connection electrodes to each other over a portion in which the first member and the second member are opposite to each other.

4 Claims, 9 Drawing Sheets

LAMINATE MOUNT ASSEMBLY

CROSS-REFERENCE TO RELATED APPLICATIONS

This application is based upon and claims the benefit of priority from Japanese Patent Application No. 2009-259165, filed on Nov. 12, 2009, the entire contents of which are incorporated herein by reference.

BACKGROUND OF THE INVENTION

1. Field of the Invention

The present invention relates to a laminate mount assembly including laminated multiple members.

2. Description of the Related Art

Conventionally, endoscopes that are inserted into a subject and that observe sites to be observed are known. Such an endoscope is configured to incorporate an electric circuit module that mounts an imaging device on the tip of a flexible elongate insertion member. By inserting the insertion member into the body cavity, a site to be observed is observed. It is desirable that the tip of the insertion member be short to reduce pain of patients. As a technology to solve this kind of problem, for example, according to Japanese Laid-open Patent Publication No. 2008-168042, size reduction is realized in a way that, while protruding electrodes are provided respectively in opposite positions on two substrates to be connected, through holes are provided in positions corresponding to the protruding electrodes on a middle substrate arranged between the substrates, and the substrates are then connected by inserting the protruding electrodes of each of the substrates into the through holes.

In addition, as a technology for reducing the size of an apparatus, as disclosed in Japanese Laid-open Patent Publication No. 8-279588, there is a technology in which a flexible multilayer wiring substrate is provided on the circumferential end surfaces of a semiconductor integrated circuit device configured by laminating and arranging multiple wiring substrates and thereby the wiring substrates are connected.

SUMMARY OF THE INVENTION

A laminate mount assembly according to an aspect of the present invention includes a first member that includes an inter-member connection electrode that is provided on an end surface that forms a predetermined inter-member connection side surface; a second member that includes an inter-member connection electrode that is provided on an end surface that forms the inter-member connection side surface, the second member being arranged to be parallel with the first member; and a conductive film that electrically connects the inter-member connection electrodes to each other over a portion in which the first member and the second member are opposite to each other.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a laminate mount assembly according to the present invention will be described below with reference to the drawings. The embodiments do not limit the invention. Like numbers refer to like elements throughout the drawings.

Figure 1:
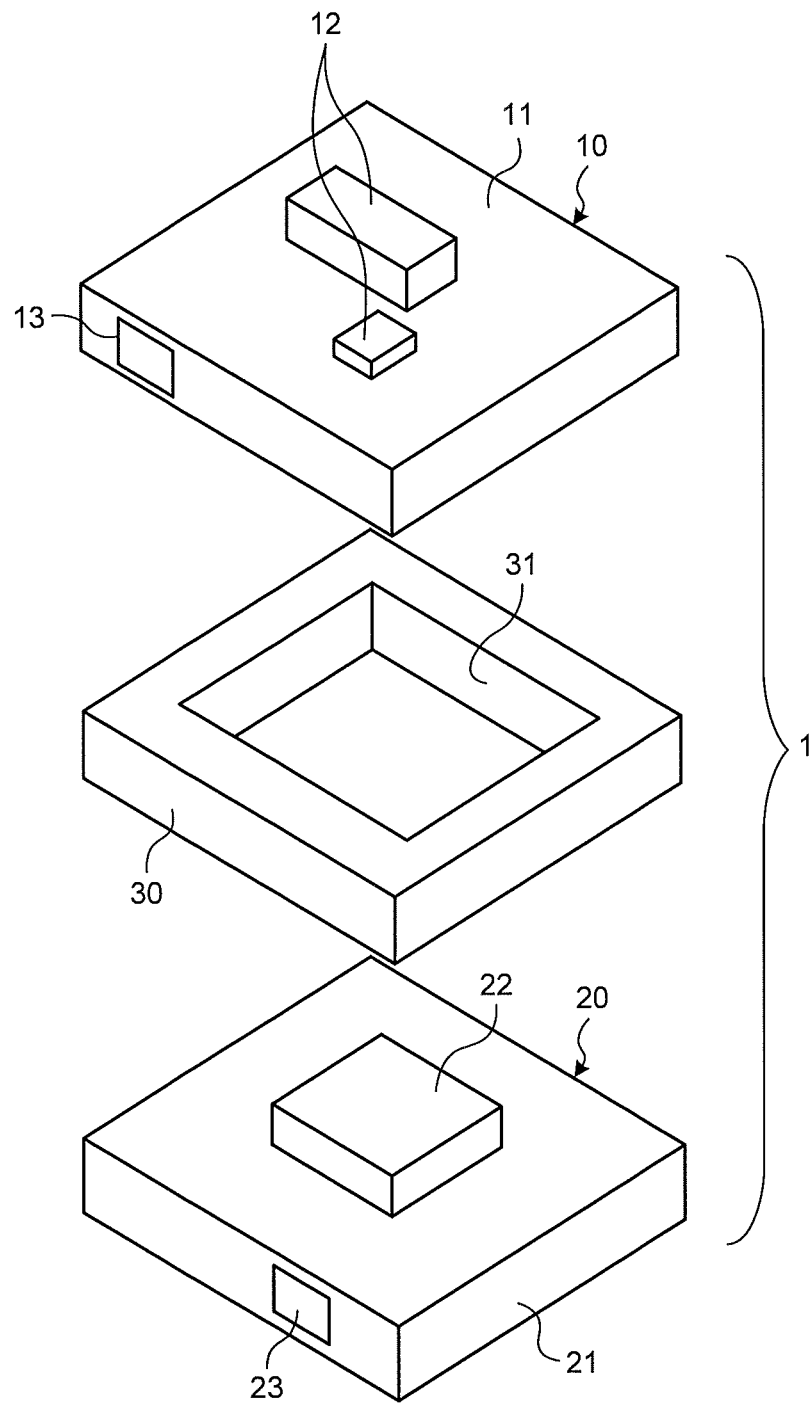
FIG. 1 is a perspective view illustrating a configuration example of a laminate mount assembly of a first embodiment.
Figure 2:
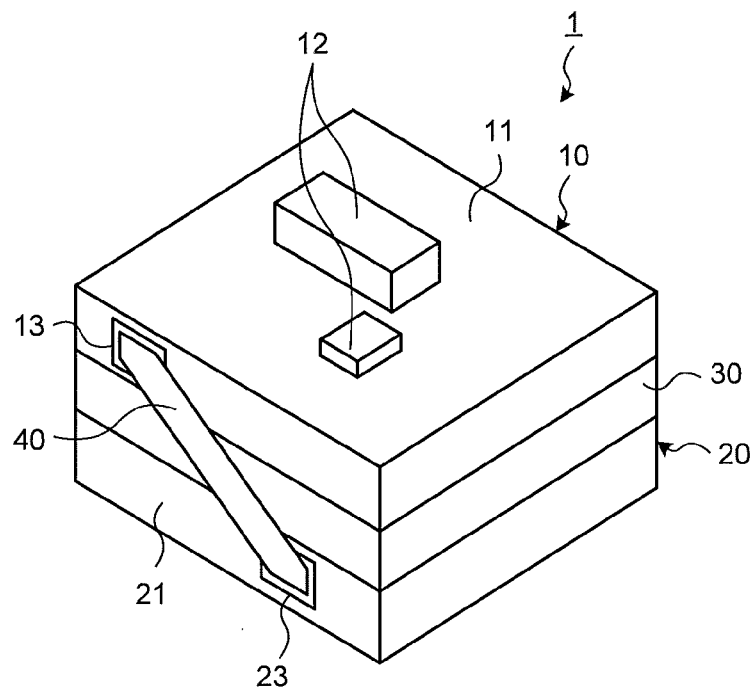
FIG. 2 is another perspective view illustrating the configuration example of the laminate mount assembly of the first embodiment.

FIGS. 1 and 2 are perspective views illustrating a configuration example of a laminate mount assembly 1 of a first embodiment. As illustrated in FIGS. 1 and 2, the laminate mount assembly 1 includes a first member 10 and a second member 20 that are parallel and are arranged to be opposite to each other and includes an intermediate member 30 that is arranged between the first member 10 and the second member 20. FIG. 1 separately illustrates each of the first member 10, the second member 20, and the intermediate member 30 that constitutes the laminate mount assembly 1. FIG. 2 illustrates a state in which the first member 10 and the second member 20 are connected to each other with the intermediate member 30 being arranged between the first member 10 and the second member 20.

The first member 10 includes a first substrate 11 that is a circuit board having the top surface serving as the right surface and on which an wiring pattern is formed. The first member 10 is configured to mount mount parts 12, such as an electric circuit, via part mount electrodes (not shown) that are provided on the top surface of the first substrate 11. A first inter-member connection electrode 13 is provided on a predetermined end surface of the first substrate 11.

Similarly, the second member 20 includes a second substrate 21 that is a circuit board and the second member 20 is configured to mount a mount part 22 via a part mount electrode (not shown) that is provided on the top surface. A second inter-member connection electrode 23 is provided on a predetermined end surface of the second substrate 21.

The first and second substrates 11 and 21 have outer shapes that are approximately the same. The first and second substrates 11 and 21 are realized as, for example, organic substrates or ceramic substrates. However, the first and second substrates 11 and 21 are not limited to this. Any substrates may be appropriately used in which the first and second inter-member connection electrodes 13 and 23 can be formed on the above-described predetermined end surfaces.

The first and second inter-member connection electrodes 13 and 23 that are respectively provided on the end surfaces of the first and second substrates 11 and 21, which constitute the first and second members 10 and 20, are for electrically connecting the first member 10 and the second member 20. When the laminate mount assembly 1 is configured by arranging the first member 10 and the second member 20 to be opposite to each other as illustrated in FIG. 2, the first and second inter-member connection electrodes 13 and 23 are provided on the end surfaces that form an identical surface (inter-member connection electrode) of the laminate mount assembly 1.

As illustrated in FIG. 1, the intermediate member 30 whose outer shape is a rectangular annular shape in a size approximately the same as that of the first and second substrates 11 and 21 of the first member 10 and the second member 20. The intermediate member 30 is formed to have a pre-set height. The height of the intermediate member 30 is previously set according to, for example, the height of the mount part 22 that is mounted on the second substrate 21 of the second member 20. The intermediate member 30 is arranged between the first and second members 10 and 20, the first and second substrates 11 and 21 of the first member 10 and the second member 20 are arranged at an interval corresponding to the height of the intermediate member 30. The space formed between the first and second substrates 11 and 21 by an opening portion 31 of the intermediate member 30 serves as a housing space for the mount part 22.

The end surfaces of the first substrate 11 of the first member 10, of the intermediate member 30, and of the second substrate 21 of the second member 20 form the side surface of the laminate mount assembly 1 as illustrated in FIG. 2. A conductive film 40 that connects the first and second inter-member connection electrodes 13 and 23 via the end surface of the intermediate member 30 is provided on the inter-member connection side surface including the end surfaces of the first and second substrates 11 and 21 on which the first and second inter-member connection electrodes 13 and 23 are formed. The conductive film 40 is formed by a coating, sputtering, applying conductive ink, or applying a conductive paste such that both of the edges of the conductive film 40 respectively overlap the inter-member connection electrode 13 and the second inter-member connection electrode 23. The thickness of the conductive film 40 is about 0.1 μm when the conductive film 40 is formed by sputtering and is about few tens of μm when the conductive film 40 is formed by a coating or applying a conductive paste.

When manufacturing the laminate mount assembly 1, the first member 10 in which the mount parts 12 are mounted on the first substrate 11 and the second member 20 in which the mount part 22 is mounted on the second substrate 21 are arranged to be opposite to each other with the intermediate member 30 being arranged between the first member 10 and the second member 20. More specifically, the intermediate member 30 is arranged between the first and second members 10 and 20 with an orientation such that the end surface of the first substrate 11, on which the first inter-member connection electrode 13 is arranged, and the end surface of the second substrate 21, on which the second inter-member connection electrode 23 is arranged, form the identical side surface of the laminate mount assembly and then the first member 10, the intermediate member 30, and the second member 20 are laminated and aligned. The first member 10, the intermediate member 30, and the second member 20 that are aligned as described above are sequentially fixed using, for example, an adhesive. It is sufficient if the members are fixed. Thus, the members may be fixed using other methods, such as anodic bonding, without an adhesive. In this case, resin may be filled as a reinforcing member in the space formed inside by the opening portion 31 of the intermediate member 30, thereby fixing and protecting the internal members. Subsequently, the conductive film 40 is arranged such that both of the ends of the conductive film 40 overlap the first inter-member connection electrode 13 and the second inter-member connection electrode 23, respectively, via the end surface of the intermediate member 30. Thereafter, a protective film may be formed to cover the conductive film 40 using a resin thereby to protect the conductive film 40 and the portions in which the conductive film 40 and the first and second inter-member connection electrodes 13 and 23 make contact.

As described above, in the first embodiment, the first and second inter-member connection electrodes 13 and 23 are provided respectively on the end surfaces of the first and second substrates 11 and 21 of the first and second members 10 and 20, which are end surfaces that form the inter-member connection side surface of the laminate mount assembly 1, and the conductive film 40 is arranged to make contact with the first and second inter-member connection electrodes 13 and 23. This electrically connects the first and second members 10 and 20. As described above, in the technology of Japanese Laid-open Patent Publication No. 2008-168042, protruding electrodes are provided respectively in opposite positions on two substrates to be connected, through holes are provided in positions corresponding to the protruding electrodes on a middle substrate arranged between the substrates, and the substrates are then connected by inserting the protruding electrodes of each of the substrates into the through holes. In contrast, in the first embodiment, the inter-member connection electrodes 13 and 23 are connected to each other by the conductive film 40 that is provided via the end surface of the intermediate member 30. For this reason, the positions in which the first and second inter-member connection electrodes 13 and 23 can be individually set if they are in the end surfaces of the first and second substrates 11 and 21 of the first and second members 10 and 20, which are end surfaces that form the inter-member connection side surface of the laminate mount assembly 1. This leads to increased freedom in designing wirings. In the technology of Japanese Laid-open Patent Publication No. 8-279588, a flexible multilayer wiring substrate is arranged on the circumferential end surfaces of a semiconductor integrated circuit device. The thickness of the flexible multilayer wiring substrate is about 100 μm. In contrast, in the first embodiment, the thickness of the conductive film 40, which is provided on the inter-member connection side surface of the laminate mount assembly 1 in order to connect the first and second inter-member connection electrodes 13 and 23, is about 0.1 μm to few tens of μm, which is smaller than the thickness of the flexible multilayer wiring substrate. Thus, the laminate mount assembly 1 is not large-sized. This leads to an effect of increased design freedom and size reduction.

In the first embodiment, the first substrate 11 in the rectangular shape is illustrated. Alternatively, instead of the first member 10, a substrate formed to be rectangular annular as the intermediate member 30 is (see a first member 10b in FIG. 4 described below) may be used.

In the first embodiment, the first and second inter-member connection electrodes 13 and 23 are provided respectively on the end surfaces of the first and second substrates 11 and 21 of the first and second members 10 and 20, which are end surfaces that form the inter-member connection side surface of the laminate mount assembly 1. Alternatively, a configuration may be employed in which inter-member connection electrodes to be connected are arranged on end surfaces of the first and second substrates, which are end surfaces that form different side surfaces of the laminate mount assembly, and a conductive film is then formed between the inter-member connection electrodes.

Figure 3:
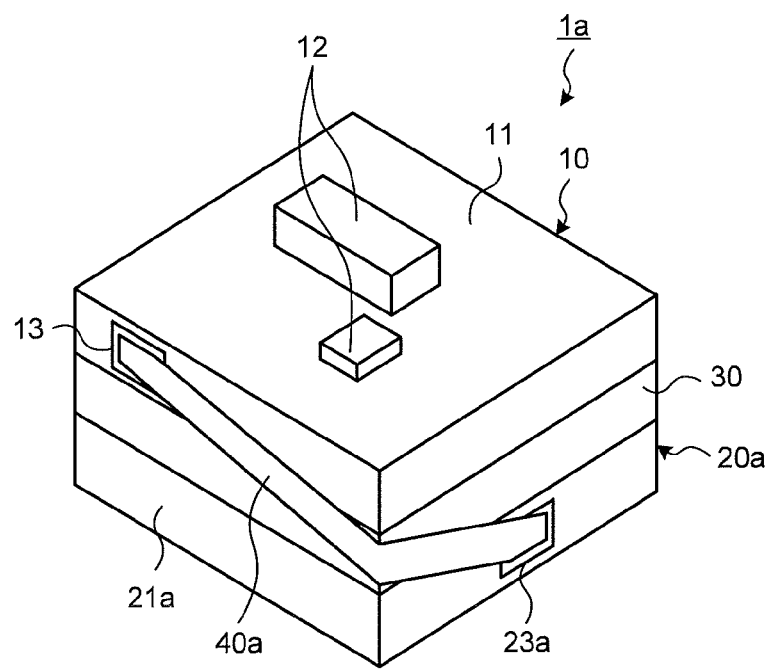
FIG. 3 is a perspective view of a configuration example of a laminate mount assembly of a modification.

FIG. 3 is a perspective view of a configuration example of a laminate mount assembly 1a of a modification. In FIG. 3, the same elements as those of the first embodiment are denoted by the same reference numerals as those of the first embodiment. In the laminate mount assembly 1a of the modification, the first inter-member connection electrode 13 is arranged on a predetermined end surface of the first substrate 11. In the laminate mount assembly 1a, a second inter-member connection electrode 23a is arranged in an end surface of a second substrate 21a, which is an end surface forming a side surface of the laminate mount assembly 1a different from the side surface of the laminate mount assembly 1a including the end surface of the first substrate 11 on which the first inter-member connection electrode 13 is arranged. In addition, a conductive film 40a is arranged to make contact with the first inter-member connection electrode 13 and the second inter-member connection electrode 23a. The conductive film 40a is formed, for example, by sputtering. Accordingly, the first and second members 10 and 20a are connected to each other.

Figure 4:
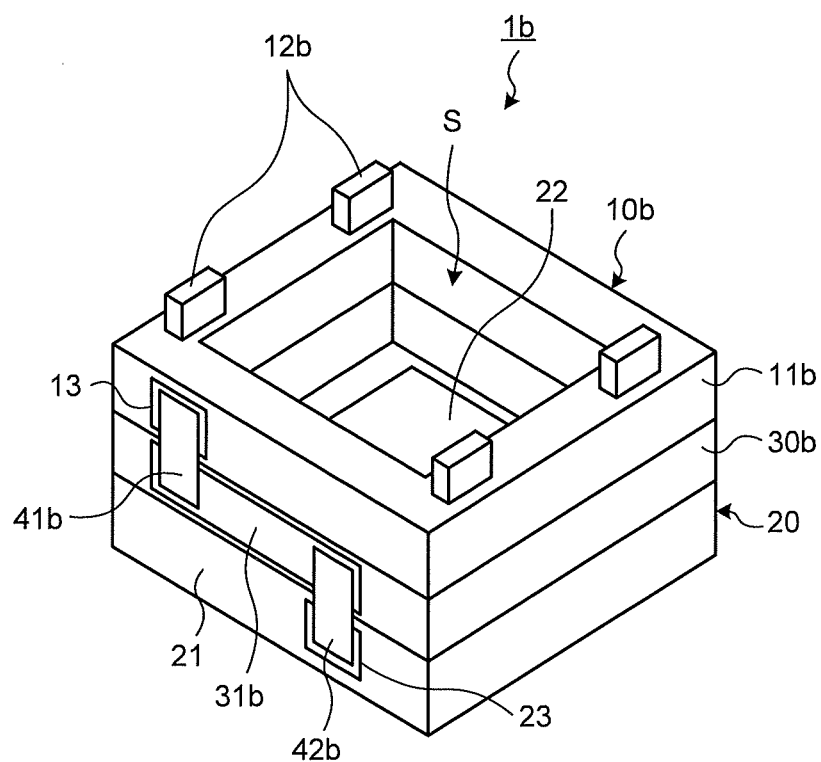
FIG. 4 is a perspective view illustrating a configuration example of a laminate mount assembly of a second embodiment.

FIG. 4 is a perspective view illustrating a configuration example of a laminate mount assembly 1b of a second embodiment. As illustrated in FIG. 4, the same elements as those of the first embodiment are denoted by the same reference numerals as those of the first embodiment. As illustrated in FIG. 4, the laminate mount assembly 1b includes the first member 10 and the second member 20 that are parallel and are arranged to be opposite to each other and includes an intermediate member 30b that is arranged between the first member 10b and the second member 20.

In the second embodiment, a first substrate 11b that constitutes the upper first member 10b is illustrated as a circuit board whose outer shape is a rectangular annular shape in a size approximately the same as that of the second member 20. An opening portion of the first substrate 11b and an opening portion of the intermediate member 30b form a housing space S for the mount part 22 that is mounted on the second substrate 21 that constitutes the second member 20. Mount parts 12b, such as an electric circuit, are appropriately mounted on the top surface of the first substrate 11b of the first member 10b.

In the second embodiment, a relay electrode 31b is provided on an end surface of the intermediate member 30b, which end surface forms an identical surface (inter-member connection side surface) of the laminate mount assembly 1b together with end surfaces of the first and second substrates 11b and 21 on which the first inter-member connection electrode 13 and the second inter-member connection electrode 23 are provided, respectively. The relay electrode 31b is rectangular and is formed along the end surface of the intermediate member 30b to have a length such that one end of the relay electrode 31b is positioned below the first inter-member connection electrode 13 and the other end is positioned above the second inter-member connection electrode 23.

A first conductive film 41b is provided such that both of the ends of the first conductive film 41b respectively overlap one end of the first inter-member connection electrode 13 and one end of the relay electrode 31b, and a second conductive film 42b is provided such that both of the ends of the second conductive film 42b respectively overlap one end of the second inter-member connection electrode 23 and the other end of the relay electrode 31b.

When manufacturing the laminate mount assembly 1b, the first member 10b in which the mount parts 12b are mounted on the first substrate 11b and the second member 20 in which the mount part 22 is mounted on the second substrate 21 are arranged to be opposite to each other with the intermediate member 30b being arranged between the first member 10b and the second member 20. More specifically, the first member 10b, the intermediate member 30b, and the second member 20 are laminated and aligned with an orientation such that the end surface of the first substrate 11b on which the first inter-member connection electrode 13 is provided, the end surface of the intermediate member 30b on which the relay electrode 31b is provided, and the end surface of the second substrate 21 on which the second inter-member connection electrode 23 is provided form the identical side surface of the laminate mount assembly 1b. The first member 10b, the intermediate member 30b, and the second member 20 that are aligned as described above are sequentially fixed using, for example, an adhesive. Subsequently, the first conductive film 41b is provided such that both of the ends of the first conductive film 41b respectively overlap the first inter-member connection electrode 13 and the relay electrode 31b, and the second conductive film 42b is provided such that both of the ends of the second conductive film 42b respectively overlap the second inter-member connection electrode 23 and the relay electrode 31b.

As described above, the second embodiment has the same effects as those of the first embodiment. The first and second inter-member connection electrodes 13 and 23 are connected via the relay electrode 31b with which the intermediate member 30b is provided. Accordingly, the length of one conductive film (the first conductive film 41b or the second conductive film 42b) can be shorter compared with the case in which the first and second inter-member connection electrodes 13 and 23 are connected using the conductive film 40 as in the case of the first embodiment. Because the first and second conductive films 41b and 42b have small thicknesses of about 0.1 μm to few tens of μm, the conductor resistance is high. Thus, the shorter the length of the conductive film is, the more the electric performance can be increased. This improves the performance of the laminate mount assembly.

In the second embodiment, the first substrate 11b in the rectangular annular shape is illustrated. Alternatively, a rectangular substrate like the first substrate 11 described in the first embodiment may be used as the first substrate 11b.

Figure 5:
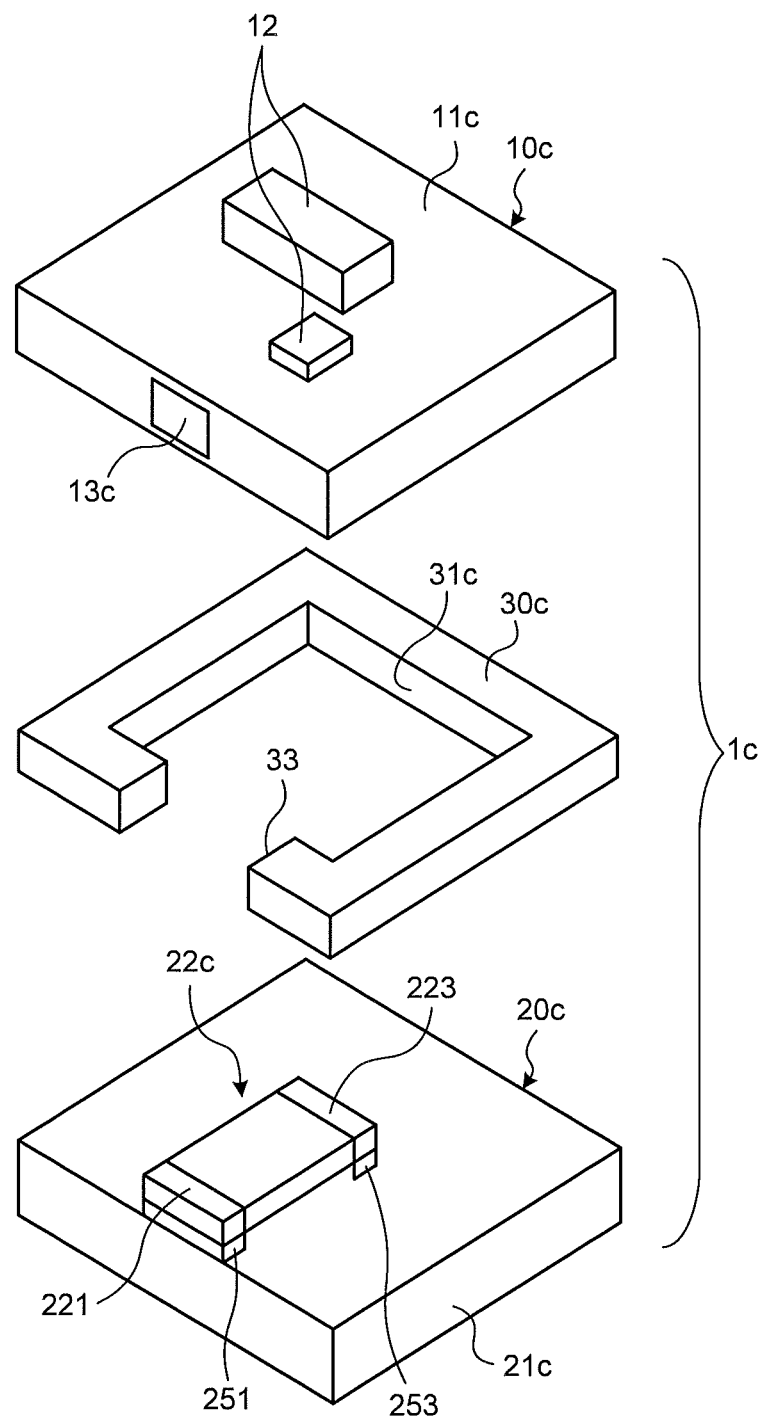
FIG. 5 is a perspective view illustrating a configuration example of a laminate mount assembly of a third embodiment.
Figure 6:
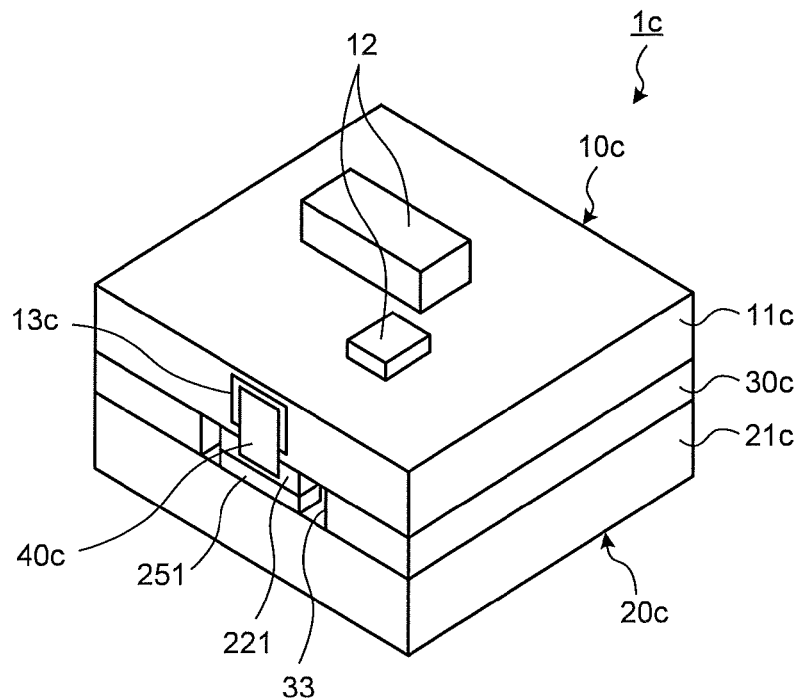
FIG. 6 is another perspective view illustrating the configuration example of the laminate mount assembly of the third embodiment.
Figure 7:
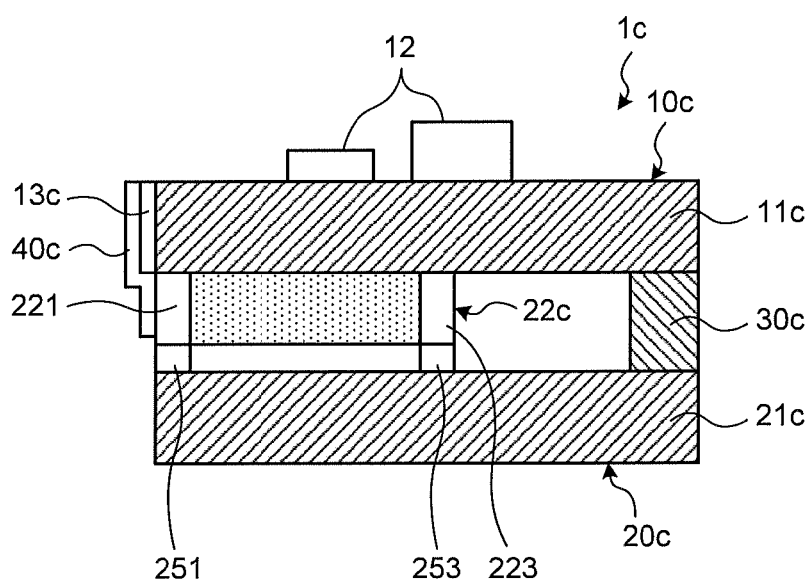
FIG. 7 is a cross-sectional view illustrating a configuration example of the laminate mount assembly of the third embodiment.

FIGS. 5 and 6 are perspective views illustrating a configuration example of a laminate mount assembly 1c of a third embodiment. FIG. 7 is a vertical cross-sectional view taken along a direction of a plane orthogonal to an inter-member connection side surface of the laminate mount assembly 1c. As illustrated in FIGS. 5 to 7, the laminate mount assembly 1c includes a first member 10c and a second member 20c that are parallel and are arranged to be opposite to each other and includes an intermediate member 30c that is arranged between the first member 10c and the second member 20c. FIG. 5 separately illustrates each of the first member 10c, the second member 20c, and the intermediate member 30c. FIG. 6 illustrates a state in which the first member 10c and the second member 20c are connected to each other with the intermediate member 30c being arranged between the first member 10c and the second member 20c.

The first member 10c includes a first substrate 11c that is a circuit board having the top surface serving as the right surface and on which an wiring pattern is formed. The first member 10c is configured to mount the mount parts 12, such as an electric circuit, via part mount electrodes (not shown) that are provided on the top surface of the first substrate 11c. A first inter-member connection electrode 13c is provided on a predetermined end surface of the first substrate 11c. The first inter-member connection electrode 13c is provided in a position above a mount part electrode 221 that is exposed from a cutout 33 to be described below.

The lower second member 20c includes a second substrate 21c that is a circuit board. Two part mount electrodes 251 and 253 for mounting a mount part 22c on the top surface of the second member 20c are provided. The part mount electrode 251, out of the part mount electrodes 251 and 253, is provided on an end portion on the side of an end surface that forms the inter-member connection side surface on which the first inter-member connection electrode 13c is provided.

The mount part 22c that is mounted on the top surface of the second substrate 21c via the part mount electrodes 251 and 253 includes two mount part electrodes 221 and 223. The side surface on which the mount part electrode 221 of the mount part 22c is provided is arranged along the inter-member connection side surface of the laminate mount assembly 1c. The bottom surfaces of the mount part electrodes 221 and 223 are connected to the part mount electrodes 251 and 253 using a conductive material, such as solder, and thus the mount part 22c is mounted on the second substrate 21c.

As illustrated in FIG. 5, the intermediate member 30c is formed to have an outer shape in a size approximately the same as those of the first member 10c and the second member 20c. In the third embodiment, the intermediate member 30c is formed to have a height approximately the same as that of the mount part 22c, which is mounted on the second substrate 21c of the second member 20c. The cutout 33 that is obtained by cutting off a part of the inter-member connection side surface of the laminate mount assembly 1c is formed in the intermediate member 30c. The cutout 33 realizes a configuration in which an opening portion 31c is partly open on the inter-member connection side surface. Accordingly, when the first member 10c, the intermediate member 30c, and the second member 20c are laminated and thus the laminate mount assembly 1c is structured, the mount part electrode 221 of the mount part 22c is exposed from the cutout 33. In the third embodiment, the mount part electrode 221 serves as an inter-member connection electrode of the second member 20c, and a conductive film 40c, with its ends respectively overlapping the first inter-member connection electrode 13c and the mount part electrode 221, is provided over the portion in which the first member 10c and the second member 20c are opposite to each other.

It is sufficient if the cutout 33 is formed according to the width of the mount part 22c along the direction of the inter-member connection side surface of the laminate mount assembly 1c. A configuration may be alternatively employed in which a member having a C-shape in a plan view is used instead of the intermediate member 30c and thus the whole area on the inter-member connection side surface of the laminate mount assembly 1c is open.

When the laminate mount assembly 1c is manufactured, the first member 10c in which the mount part 12 is mounted on the first substrate 11c and the second member 20c in which the mount part 22c is mounted on the second substrate 21c are arranged to be opposite to each other with the intermediate member 30c being arranged between the first member 10c and the second member 20c. More specifically, the first member 10c, the intermediate member 30c, and the second member 20c are laminated and aligned with an orientation such that the end surface of the first substrate 11c on which the first inter-member connection electrode 13c is provided, the end surface of the intermediate member 30c in which the cutout 33 is formed, and the end surface of the second substrate 21c on which the second mount part 22c is mounted form the identical side surface of the laminate mount assembly 1c. The first member 10c, the intermediate member 30c, and the second member 20c that are aligned as described above are sequentially fixed using, for example, an adhesive. Subsequently, the conductive film 40c is provided such that both of the ends of the conductive film 40c respectively overlap the first inter-member connection electrode 13c and the mount part electrode 221 exposed from the cutout 33.

As described above, the third embodiment has the same effects as those of the first embodiment. In addition, according to the third embodiment, the bottom surface of the mount part electrode 221 is connected to the part mount electrode 251 provided on the end portion on the top surface of the second substrate 21c, which is an end portion on the side of the inter-member connection side surface, and the mount part electrode 221 is exposed to the inter-member connection side surface of the laminate mount assembly 1c so that the mount part electrode 221 can be connected to the first inter-member connection electrode 13c via the conductive film 40c. This shorten the wiring pattern compared to the case in which inter-member connection electrodes that are provided on substrates as in the first embodiment are connected to each other. Accordingly, the electric performance can be improved.

In the third embodiment, the first substrate 11c having a rectangular shape is illustrated. Alternatively, instead of the first substrate 11c, a substrate formed to be rectangular annular as the first substrate 11b shown in FIG. 4 is may be used.

A configuration may be employed in which the upper first member mounts a mount part such that a mount part electrode is exposed to the inter-member connection side surface as in the case of the second member 20c. A configuration may be employed in which the mount part electrode of this mount part is used as an inter-member connection electrode of the first member and a conductive film is provided between the mount part electrode and the inter-member connection electrode of the second member and accordingly the mount part electrode and the inter-member connection electrode are connected to each other.

Figure 8:
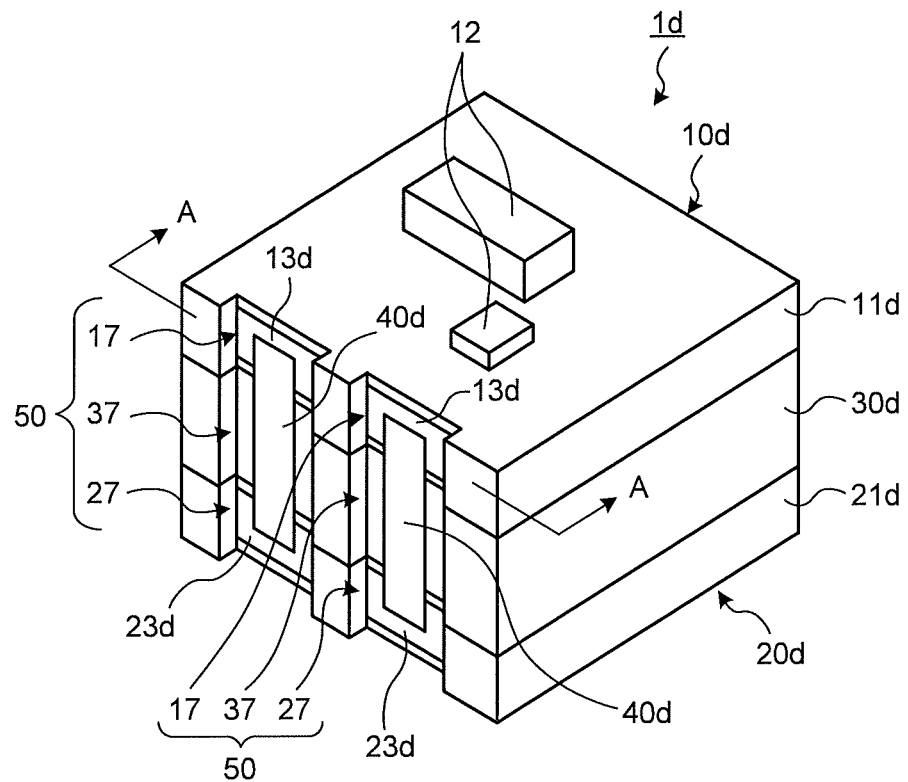
FIG. 8 is a perspective view illustrating a configuration example of a laminate mount assembly of a fourth embodiment.

FIG. 8 is a perspective view illustrating a configuration example of a laminate mount assembly 1d of a fourth embodiment. In FIG. 8, the same elements as those of the first embodiment are denoted by the same reference numerals as those of the first embodiment. As illustrated in FIG. 8, as in the case of the first embodiment, the laminate mount assembly 1d includes a first member 10d and a second member 20d that are parallel and are arranged to be opposite to each other and includes an intermediate member 30d that is arranged between the first member 10d and the second member 20d.

In the fourth embodiment, two concave portions 17 are formed on an end surface of a first substrate 11d that configures the first member 10d, two concave portions 27 are formed on an end surface of the intermediate member 30d, and two concave portions 37 are formed on an end surface of a second substrate 21d that configures the second member 20d. The concave portions 17, 27, and 37 form two grooves 50 continuous vertically on an inter-member connection side surface of the laminate mount assembly 1d. A first inter-member connection electrode 13d is provided on a side portion of each of the two concave portions 17 of the first substrate 11d and a second inter-member connection electrode 23d is provided on a side portion of each of the two concave portions 27 of the second substrate 21d.

The concave portions 17, 27, and 37 are formed by cutting the corresponding end surfaces of the first and second substrates 11d and 21d using, for example, a drill or laser radiation. The widths of the concave portions 17, 27, and 37 are set according to the width of a conductive film 40d to be provided. The depths of the concave portions 17, 27, and 37 are set to be larger than a sum of the thickness of the first and second inter-member connection electrodes 13d and 23d, which are provided on the side portions of the concave portions 17 and 27 of the first substrate 11d and the second substrate 21d, and the thickness of the conductive film 40d, which is provided on the concave portions 17, 27, and 37 as described below.

In the fourth embodiment, the conductive films 40d are provided in the grooves 50 that are formed by the concave portions 17, 27, and 37. The conductive film 40d is provided by, for example, applying an amorphous material, such as conductive paste or conductive ink.

Figure 9:
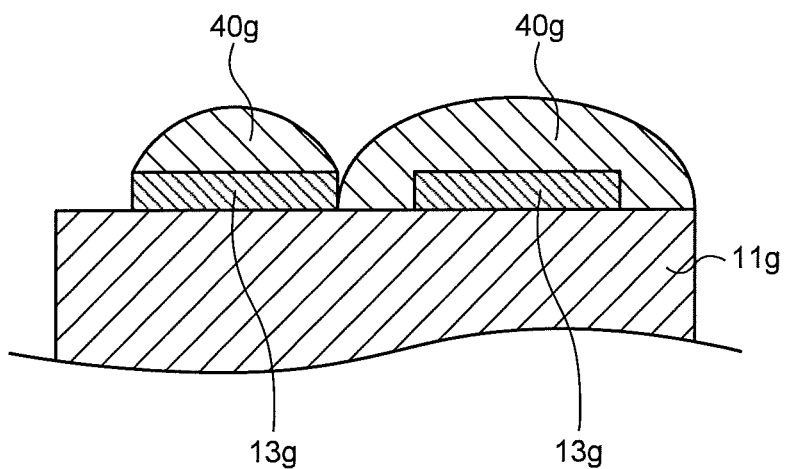
FIG. 9 is a cross-sectional view of portions in each of which a first inter-member connection electrode, which is provided on a first substrate in which no concave portion is formed, and a conductive film are connected to each other.

A case in which no concave portion is formed on the inter-member connection side surface and the case in which the concave portions 17, 27, and 37 are formed as in the case of the fourth embodiment will be described with reference to FIGS. 9 and 10. FIG. 9 is a cross-sectional view of connection portions in each of which a first inter-member connection electrode 13g that is provided on a first substrate 11g, on which no groove portion is formed, and a conductive film 40g are connected to each other. In contrast, FIG. 10 is a cross-sectional view of FIG. 8 taken along the line A-A (a cross-sectional view of portions in each of which the first inter-member connection electrode 13d, which is provided on the first substrate 11d on which the concave portions 17, 27, and 37 are formed, and the conductive film 40d are connected to each other).

When multiple combinations of first and second inter-member connection electrodes are formed in a predetermined inter-member connection side surface and the first and second inter-member connection electrodes are connected via conductive films, if no concave portion is not formed on the inter-member connection side surface, the conductive films 40g, which connects the first and second inter-member connection electrodes of each combination, may make contact with each other as illustrated in FIG. 9. This leads to a problem of short circuiting. Particularly, this is problematic when the interval between adjacent first inter-member connection electrodes, or between adjacent second inter-member connection electrodes, is narrow or when conductive films are provided by applying an amorphous material as described above.

Figure 10:
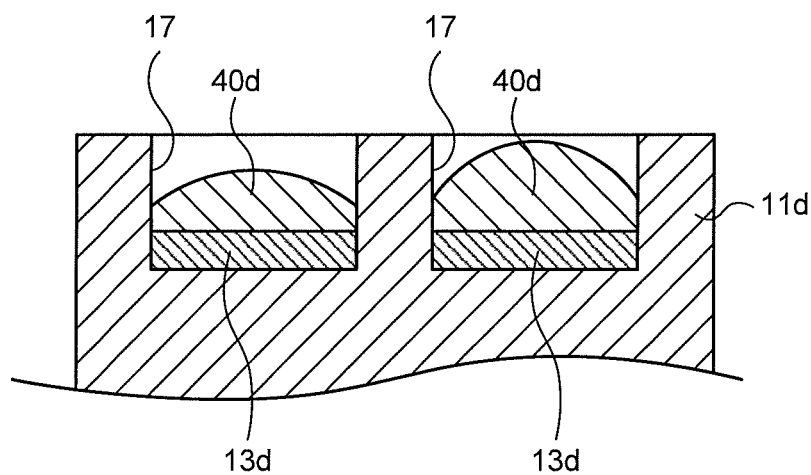
FIG. 10 is a cross-sectional view of FIG. 8 taken along the line A-A.

In contrast, in a configuration in which, the concave portions 17, 27, and 37 (FIG. 10 illustrates the concave portions 17 only) are formed on the inter-member connection side surface as in the case of the laminate mount assembly 1d of the fourth embodiment illustrated in FIG. 10, the areas in each of which the conductive film 40d that connects first and second inter-member connection electrodes of each combination is provided can be separated from each other. Accordingly, even if the amount or viscosity of the amorphous material to be applied varies more or less, a situation does not occur in which, pieces of the material make contact with each other and thus short circuiting is caused. Accordingly, even when the conductive films 40d are provided by applying an amorphous material, multiple combinations of first and second inter-member connection electrodes can be provided densely and can be connected assuredly. This simplifies control on application conditions (for example, the amount or viscosity).

In the fourth embodiment, the first substrate 11d having a rectangular shape is illustrated. Alternatively, instead of the first substrate 11d, a substrate formed to be rectangular annular as the first substrate 11b illustrated in the second embodiment is may be used.

Figure 11:
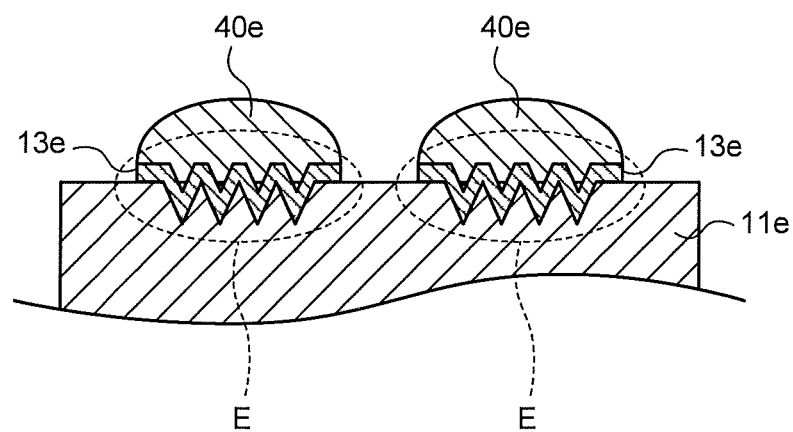
FIG. 11 is a cross-sectional view of portions in each of which a first inter-member connection electrode and a conductive film are connected to each other in a laminate mount assembly of a fifth embodiment.

FIG. 11 is a cross-sectional view of portions in each of which a first inter-member connection electrode 13e of a first substrate 11e, which constitutes a first member of a laminate mount assembly, and a conductive film 40e are connected to each other according to a fifth embodiment. As illustrated in FIG. 11, in the fifth embodiment, the right surfaces of the first inter-member connection electrodes 13e have asperities. The asperities are obtained in a way that asperities are formed at least in areas E in each of which the first inter-member connection electrode 13e is to be provided in the end surface of the first substrate 11e, which is an end surface forming an inter-member connection side surface, and then the first inter-member connection electrodes 13e are provided in the areas E in which the asperities are formed. The asperities can be formed using a proper method, such as sand blasting or mechanical processing. The asperities may be obtained in a way that a first inter-member connection electrode is provided on a flat first substrate and then sand blasting or mechanical processing is performed on the right surface of the first inter-member connection electrode.

Although it is not illustrated in the drawings, a second substrate that constitutes a second member of the laminate mount assembly of the fifth embodiment is similarly provided with second inter-member connection electrodes each having asperities on their right surfaces. The conductive films 40e are then each provided between the first inter-member connection electrode 13e with the right surface having asperities and a second inter-member connection electrode (not shown) and thus the first and second inter-member connection electrodes are connected to each other.

A configuration may be employed in which asperities are formed in an area in which the conductive film 40e is provided similarly in an end surface of an intermediate member of the laminate mount assembly of the fifth embodiment, which is an end surface forming the inter-member connection side surface.

The fifth embodiment has the same effects as those of the first embodiment, and the area in which the first inter-member connection electrode 13e and the second inter-member connection electrode make contact with the conductive film 40e can be increased, which increases their adhesion strength. Accordingly, a more reliable laminate mount assembly can be obtained.

Figure 12:
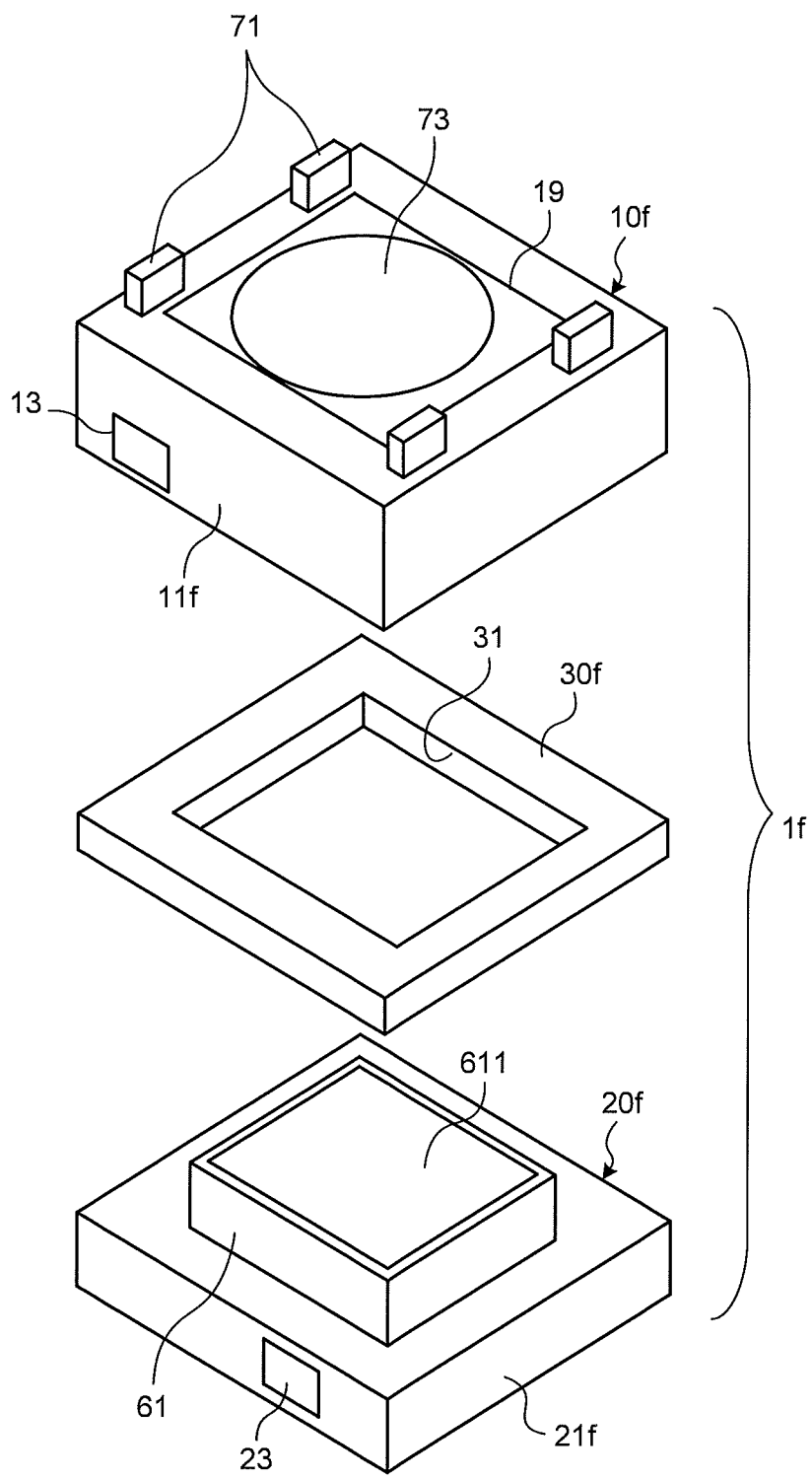
FIG. 12 is a perspective view illustrating a configuration example of a laminate mount assembly of a sixth embodiment.
Figure 13:
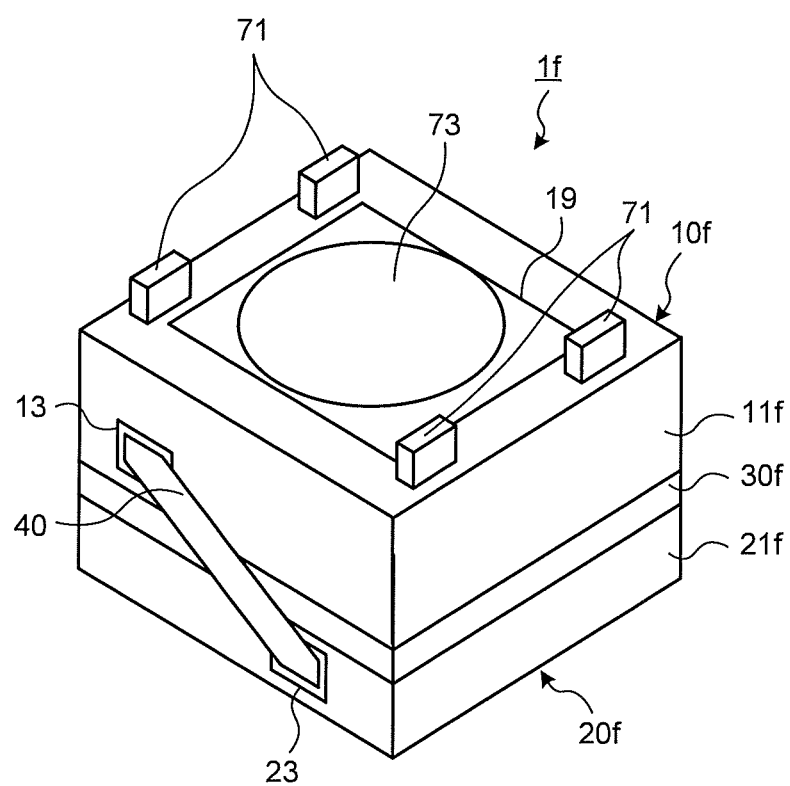
FIG. 13 is another perspective view illustrating the configuration example of the sixth embodiment.

FIGS. 12 and 13 are perspective views illustrating a configuration example of a laminate mount assembly 1f of a sixth embodiment. The laminate mount assembly 1f mounts electric parts, such as an imaging device, as mount parts. In other words, as illustrated in FIG. 12, the laminate mount assembly 1f includes, as in the case of the first embodiment, a first member 10f and a second member 20f that are parallel and are arranged to be opposite to each other and includes an intermediate member 30f that is arranged between the first member 10*f* and the second member 20*f*. FIG. 12 separately illustrates the first member 10*f*, the second member 20*f*, and the intermediate member 30*f* that constitute the laminate mount assembly 1*f*. FIG. 13 illustrates a state in which the first member 10*f* and the second member 20*f* are connected to each other with the intermediate member 30*f* being arranged between the first member 10*f* and the second member 20*f*.

In the sixth embodiment, the upper first member 10*f* includes a first substrate 11*f* whose outer shape is a rectangular annular shape in a size approximately the same as that of the second member 20*f*, and a lens 73 is fitted to an opening portion 19 so that an optical function area is formed. The first substrate 11*f* mounts LEDs 71 and other necessary electric parts (not shown) via part mount electrodes (not shown) on the top surface of the first substrate 11*f*. The first inter-member connection electrode 13 is provided on a predetermined end surface of the first substrate 11*f*.

In contrast, the lower second member 20*f* includes a second substrate 21*f*, and an imaging device 61 is mounted via a part mount electrode (not shown) provided on the top surface of the second member 20*f* so that an optical function area is formed. In addition to the imaging device 61, necessary electric parts (not shown) are mounted on the second substrate 21*f*. A second inter-member connection electrode 23 is provided on a predetermined end surface of the second substrate 21*f*. The imaging device 61 has a light receiving surface 611. The imaging device 61 is mounted on the top surface of the second member 20*f* with the light receiving surface 611 facing upward.

As in the case of the first embodiment, the first and second inter-member connection electrodes 13 and 23 that are provided on the end surfaces of the first and second substrates 11*f* and 21*f*, which constitute the first member 10*f* and the second member 20*f*, are connected to each other by providing the conductive film 40 as illustrated in FIG. 13. The connection is not limited to the first embodiment. A configuration of another embodiment, such as the second embodiment, may be employed in order to connect the first and second inter-member connection electrodes 13 and 23 to each other.

As described above, the sixth embodiment has the same effects as those of the first embodiment, and the lens 73 is fitted to the first member 10*f* so that the optical function area is formed. Furthermore, the laminate mount assembly 1*f* having an imaging function can be obtained in a way that the optical function area is formed by mounting the imaging device 61 on the second member 20*f* and then the first member 10*f* and the second member 20*f* are laminated with the intermediate member 30*f* being arranged between the first member 10*f* and the second member 20*f*. The laminate mount assembly 1*f* can be used for, for example, endoscopes.

In the sixth embodiment, the first substrate 11*f* is a rectangular annular substrate, the lens 73 is fitted to the opening portion 19 so that the optical function area is formed on the first member 10*f*, and the imaging device 61 is mounted on the second substrate 21*f* so that the optical functional area is formed. Alternatively, a configuration may be employed in which an optical function area is formed in at least any one of the first member 10*f*, the second member 20*f*, and the intermediate member 30*f*. As an example, for example, a lens is fitted to the opening portion 31 of the intermediate member 30*f* to form an optical function area. Alternatively, a predetermined lens is fitted to each of the first member 10*f* and the intermediate member 30*f* to form optical function areas.

In each of the above-described embodiments, the case is described in which first and second members in which mount parts are mounted on circuit boards. A case in which first and second members are connected to each other as circuit boards, a case in which a circuit board is connected to a member, such as an electric circuit module, and a case in which two electric parts are laminated and connected to each other are similarly employed. A case in which more than three circuit boards are connected and a case in which more than three electric parts and electric circuit modules are laminated and connected can be similarly employed.

In each of the above-described embodiments, the configuration is illustrated in which the first and second inter-member connection electrodes provided on the end surfaces of the first and second substrates, which form the first and second members, are connected to each other on one side surface of a laminate mount assembly. Alternatively, a configuration may be employed in which first and second inter-member connection electrodes are provided on multiple end surfaces of first and second substrates and the first and second inter-member connection electrodes are connected via a conductive film on each of the end surfaces. In the first, second, third, and sixth embodiments, one first inter-member connection electrode and one second inter-member connection electrode are provided respectively on end surfaces of the first and second substrates that constitutes the first and second members. Alternatively, a configuration may be employed in which more than two first inter-member connection electrodes and more than two second inter-member connection electrodes are provided. In this case, depending on the positional relationship between the first and second inter-member connection electrodes, conductive films that connect corresponding first and second inter-member connection electrodes may intersect with each other. In this case, it is satisfied if, after the first and second inter-member connection electrodes of one set are connected via a conductive film, an insulation film is provided near at least the intersection position of the conductive films and then the first and second inter-member connection electrodes of another set are connected via a conductive film.

In the laminate mount assembly according to the present invention, inter-member connection electrodes are provided respectively on end surfaces of first and second members that form a predetermined inter-member connection side surface of the laminate mount assembly, and the conductive film that electrically connects the inter-member connection electrodes with each other is provided over a portion in which the first member and the second member are opposite to each other. Accordingly, the positions in which the inter-member connection electrodes are provided can be individually set for each of the first and second members if they are in the end surfaces that form the inter-member connection side surface. The inter-member connection electrodes are connected via the conductive film and thus, by forming the conductive film to be thin, size reduction can be realized. This leads to increased design freedom and size reduction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A laminate mount assembly comprising:
  a first member that includes an inter-member connection electrode that is provided on an end surface that forms a predetermined inter-member connection side surface;
  a second member, the second member being arranged to be parallel with the first member, the second member includes a substrate that is provided with a part mount electrode on an end portion on an upper surface of the substrate on a side of the end surface on which an inter-member connection electrode is formed, and a mount part that includes a mount part electrode provided on at least any one side surface of the mount part;

a conductive film that electrically connects the inter-member connection electrode of the first member to the mount part electrode of the mount part; and an intermediate member that is arranged between the first member and the second member, the intermediate member having a cutout portion, wherein the mount part is configured to fit within the cutout portion.

2. The laminate mount assembly according to claim 1, wherein an area in which the conductive film is provided on in inter-member connection side surface is formed as a groove-like concave portion.

3. The laminate mount assembly according to claim 1, wherein the predetermined inter-member connection side surfaces of the inter-member connection electrodes in contact with the first member or mount part have asperities.

4. The laminate mount assembly according to claim 1, wherein at least one of the first member and the second member has an optical function area.

\* \* \* \* \*